United States Patent [19]
Galimberti et al.

[11] Patent Number: 5,620,760
[45] Date of Patent: Apr. 15, 1997

[54] SHAPED ARTICLES FOR BIOMEDICAL USE

[75] Inventors: Maurizio Galimberti, Milan; Emilio Martini, Sasso Marconi; Enrico Albizzati, Arona, all of Italy

[73] Assignee: Montell Technology Company BV, Hoofddorp, Netherlands

[21] Appl. No.: 557,925

[22] Filed: Nov. 14, 1995

Related U.S. Application Data

[63] Continuation-in-part of Ser. No. 85,009, Jun. 29, 1993, abandoned.

[30] Foreign Application Priority Data

Jun. 30, 1992 [IT] Italy .................. MI92A1593

[51] Int. Cl.$^6$ .................................... B29D 23/00
[52] U.S. Cl. ............... 428/35.5; 428/36.9; 525/323; 525/324; 526/280; 526/281; 526/335; 526/340.3; 526/348; 526/348.2; 526/348.6; 604/264
[58] Field of Search .................. 525/323, 324, 525/240; 428/35.5, 36.9; 604/264; 526/160, 280, 281, 335, 340.3, 348.2, 348.6

[56] References Cited

U.S. PATENT DOCUMENTS

| | | | |
|---|---|---|---|
| 4,335,225 | 6/1982 | Collette et al. | 525/240 |
| 4,386,179 | 5/1983 | Sterling | 524/269 |
| 4,536,549 | 8/1985 | Hattori et al. | 525/240 |
| 4,540,416 | 9/1985 | Hattori et al. | 525/240 |
| 4,677,172 | 6/1987 | Zimmermann et al. | 525/323 |
| 4,818,785 | 4/1989 | Otawa et al. | 525/240 |
| 5,196,496 | 3/1993 | Galimberti et al. | 526/348.6 |

FOREIGN PATENT DOCUMENTS

| | | |
|---|---|---|
| 0287482 | 10/1988 | European Pat. Off. . |
| 2537981 | 6/1984 | France . |
| 2053246 | 2/1981 | United Kingdom . |

OTHER PUBLICATIONS

Derwent Abstract and Family Search for FR-A-2537 981.
Derwent Abstract and Family Search for EP-A-287 482.
European Search Report.

*Primary Examiner*—Mark L. Warzel
*Attorney, Agent, or Firm*—Bryan Cave L.L.P.

[57] ABSTRACT

Shaped articles for biomedical use characterized by a good transparency and flexibility also at low temperatures are prepared starting from elastomeric copolymers of ethylene with propylene and/or other alpha-olefins having a unique set of mechanical properties and thermoplastic processability. Of particular interest are devices for containing, administering, draining and transport of blood and biological and physiological fluids, syringe seals and similar applications.

7 Claims, No Drawings

SHAPED ARTICLES FOR BIOMEDICAL USE

This is a continuation-in-part of U.S. application Ser. No. 08/085,009, field Jun. 29, 1993, now abandoned.

The present invention relates to shaped articles, for biomedical use prepared starting from a new polymeric material.

The material most used for the manufacturing of flexible devices for biomedical use is represented by plastified PVC. High flexibility characteristics of the plastified PVC are due to plasticizers contained in it.

The migration and extractability of plasticizers in biologic liquids, with consequent negative effects on the health of the patient because of the toxicity of plasticizers, represent an essential problem for PVC that until now has not yet been solved. Furthermore, the extraction of plasticizers worsens the mechanical properties of PVC and diminishes its flexibility.

In addition, it has to be kept in mind the problem of the surface migration of additives based on organopolysiloxane oils used in PVC as external lubricant to give to the PVC surface a critical surface tension in order to avoid blood coagulation phenomena. Organosiloxane compounds in fact have the tendency to bleed from the PVC surface thus giving rise to problems deriving from their poor compatibility with blood (see European Patent Application EP-A-0287482).

Therefore, the need for materials which may replace PVC in these fields is felt.

Other materials useable for manufacturing flexible devices for biomedical use are styrene-ethylene-butene-styrene (SEBS) block copolymers. SEBS modified by polysiloxanes have been suggested for example as substitutive of PVC and silicone resins for the realization of some devices, such as endotracheal tubes (U.S. Pat. No. 4,386,179).

These copolymers combine good properties of optical transparency and flexibility also at low temperatures.

U.S. Pat. No. 4,335,225 describes the preparation of high molecular weight polypropylene having elastomeric characteristics and processable by technologies for thermoplastic materials and proposes a possible use for this material in the manufacture of some articles for biomedical use. The polymerization is carried out by using as catalyst the reaction product of an organic derivative of zirconium, generally tetraneophilzirconium, with a hydroxylated alumina. However, the aluminium content in the polymer which is obtained is very high, higher than 1000 ppm. The above mentioned materials till now have not found any significant application in the biomedical field.

Now it has been unexpectedly found a new polymeric material suitable for the manufacture of articles for biomedical applications which combines a good set of mechanical properties with good optical properties, and that furthermore does not present problems deriving from the extractability of metals in bologic fluids.

The material consists of elastomeric copolymers of ethylene with propylene and/or other alpha-olefins or polyenes having an ethylene content comprised between 45 and 85% by mols, preferably between 50 and 75% by mols, propylene and/or alpha olefins $CH_2=CHR$, wherein R is an alkyl radical having 2–10 carbon atoms, content between 15 and 55% by mols, preferably between 25 and 50% by mols, and diene or polyene content between 0 and 10% by mols, characterized by the following properties:
solubility in pentane at 25° C. higher than 90%;
substantial absence of crystallinity (melting enthalpy lower than 20 J/g);
content of propylene units or units deriving from the alpha-olefin in form of triads comprised between 4 and 50% of propylene or alpha olefin and at least 70% of said triads showing isotactic structure;
random distribution of ethylene and propylene units and/or units deriving from alpha-olefins in segments of the chain having copolymeric structure (values of the product of reactivity ratios of ethylene and propylene or alpha-olefin comonomers comprised between 0.4 and 1).

Copolymers have intrinsic viscosity higher than 1.5 dl/g, preferably higher than 2 dl/g and generally comprised between 2.5 and 3.5 dl/g. Particularly preferred are copolymers having an intrinsic viscosity between 2.5 and 3.0 dl/g.

As used herein, the term "intrinsic viscosity" means intrinsic viscosity [η] determined according to the following procedure:

A weighed amount of the polymer is dissolved in 50 ml of tetrahydronaphthalene (THN) solvent at 135° C. The flow time of this dilute solution and that of the pure THN solvent are determined in a level viscometer which is thermostatted at 135° C. The flow time of the solution and that of the pure solvent (THN) so obtained, are used to calculate the intrinsic viscosity [η], according to the equation:

$$\eta_{sp}/Cs = [\eta] + K'[\eta]^2 \cdot Cs$$

where:

[η]=intrinsic viscosity

K'=constant (0.35 for olefin polymers at 135° C. in THN)

Cs=(Ws/Vd)·(d2/d1)·100

Ws=sample weight (g) of the polymer used to make the solution

Vd=solvent volume (ml) at room temperature d1=solvent density at room temperature d2=solvent density at 135° C.

$$\eta_{sp} = (Fs-Fo)/Fo$$

Fs=flow time of the solution

Fo=flow time of the pure solvent

The content of diene or polyene units is preferably comprised between 0.5 and 5% by mols.

Copolymers can be transformed into manufactured articles by usual manufacturing—processes of thermoplastic materials (moulding, extrusion, injection, etc.) and relative manufactured articles are endowed with elasto-plastic properties particularly interesting for biomedical articles. High elasto-plastic properties of copolymers are made clear by low tension set values at 200%, 1 min., 25° C. (values are lower than 30%, and generally comprised between 10 and 20%) and by the high ultimate tensile strength at 4 MPa and generally comprised between 5 and 10 MPa. The mentioned values relate to tests carried out according to ASTM D412.

Optical properties are evaluated by measuring, on a plate having 1 mm thickness, the quantity of transmitted light which deviates from the original incidence angle ("haze"). Copolymers used for the preparation of the shaped articles—of the invention are characterized by haze values generally lower than about 40%, preferably lower than about 25%.

Copolymers are prepared by polymerization of ethylene with propylene and/or an alpha-olefin $CH_2=CHR$, wherein R is an alkyl having from 2 to 10 carbon atoms, optionally in the presence of a diene or polyene, with chiral catalysts obtained from metallocene derivatives of zirconium, such as ethylene bis-(tetrahydroindenyl) zirconium dichloride or dimethylsilanylen-bis-tetrahydroindenyl)-zirconium dichloride and from tetraisobutyl-alumoxane, according to what is described in Italian Patent application MI-92-A-000666, as is presented below:

Ethylene-bis(tetrahydroindenyl)-zirconium dichloride ($EBTHIZrCl_2$) is prepared by following the method described in H. H. Britzinger et al., J. Organomet. Chem., 288, p. 63, (1985).

Tetraisobutylalumoxane (TIBAO) is prepared as described in Example 2 of EP-A-384171.

To a weighed amount of $EBTHIZrCl_2$, toluene is added at a volume rate of 2 ml per each mg of metallocene. To that solution, a solution of TIBAO in toluene is added in such that the values of the Al/Zr ratio and of the molar Al concentration is as reported in Table 2. The reaction mixture is stirred at temperatures and for time periods reported in Table 2.

TABLE 2

| Example No. | Zr (mmol·$10^{-3}$) | TIBAO (Al mmol) | Al/Zr (molar ratio) | Catalyst preparation | | | Polymerization | | | | | | |
|---|---|---|---|---|---|---|---|---|---|---|---|---|---|
| | | | | Al (mmol/l) | Al ([M]) | T (°C.) | t (min) | $C_2$ in liquid phase (wt %) | $C_2$ pressure (bar) | $H_2$/gas (mol %) | P tot. (bar) | t (min) | Yield (g) | Activity $Kg_{pol}/g_{zr}$ |
| 1 | 4.69 | 9.5 | 2026 | 3.6 | 0.8 | 20 | 20 | 18 | 15.2 | 0.1 | 34.8 | 240 | 641 | 1498.6 |
| 2 | 4.69 | 9.5 | 2026 | 3.6 | 0.8 | 40 | 20 | 18 | 15.2 | 0.1 | 34.8 | 240 | 263 | 614.9 |
| 3 | 1.17 | 4.75 | 4088 | 1.8 | 0.6 | 20 | 20 | 18 | 15.2 | 0.1 | 34.8 | 120 | 190 | 1780.2 |
| 4 | 4.69 | 9.5 | 2026 | 3.61 | 0.20 | 20 | 50 | 18 | 15.2 | — | 34.8 | 240 | 400 | 936.2 |
| 5* | 11.72 | 9.5 | 810 | 3.58 | 0.51 | 20 | 10 | 17.8 | 15.2 | 0.1 | 34.8 | 300 | 620 | 579.8 |

*Terpolymerization carried out with ethyliden-norbornene; 0,87% by weight in the polymerization mixture; 21,1 g is gradually fed during the course of the polymerization.

A 4 liter steel autoclave equipped with a stirrer, pressure gauge, thermometer, catalyst loading system, monomer feeding lines and thermostatting jacket, is used. The autoclave is purged with propylene. Two liters of propylene and ethylene are charged to the autoclave until the desired pressure is reached therein. Hydrogen is added until it reaches a concentration of 0.1% by mol in the gas phase in the mixture. The toluene solution containing the catalytic system, prepared as described above, is then injected.

The polymerization is carried out at 50° C., with the total pressure kept constant by feeding ethylene. The polymerization conditions are reported in Table 2. At the end of the polymerization, the polymer is recovered by removing any unreacted monomers and is dried under vacuum.

The copolymerization is carried out in liquid phase consisting of propylene and/or alpha-olefin, working at a temperature of about 40° and 50° C.

Useable alpha olefins are, for example, butene-1, pentene-1, 4-methyl-pentene-1, hexene-1, octene-1, dodecene-1. Dienes or polyenes useable are preferably selected among linear non conjugated diolefins, such as 1,4-hexadiene, or cyclic haying and internal bridge, such as 5-ethyliden-2-norbornene.

Copolymers obtained are characterized by a very low content of metals; generally the quantity of zirconium is lower than about 1 ppm and the quantity of aluminium is lower than 500 ppm and it is generally comprised between 40 and 100 ppm. However, it is possible to obtain copolymers having even lower residue quantities of metals. Furthermore, metals contained are practically not extractable by contact with biological fluid, which is particularly advantageous in biomedical applications.

These copolymers show a unique combination of properties, in particular flexibility at low temperatures (–40° C.

and lower), thermoplastic processing and optical transparency. Furthermore, these copolymers have a good compatibility with blood and soft tissue.

In view of these properties, copolymers are particularly suitable for the manufacture of articles for biomedical applications.

For biomedical applications articles are meant those articles intended for the contact with biologic fluid or injectable. Examples of manufactured articles according to this invention are tubes for enteral and parenteral feeding, tubes for peristaltic pumps, catheters, devices for hemodialysis, bags for blood or plasma, syringe seals, artificial organs and similar applications.

Owing to the transparency characteristics of copolymers used for the preparation of the articles object of the invention, (haze values even lower than 20%), devices for containing, administering, draining and conveying of blood and physiologic fluids, such as intravenous catheters, tubes for dialysis, bags for blood and physiologic solutions and similar applications are particularly interesting. In fact it is easy to detect inside the device the presence of bubbles, blood clots, scales of biomineral source in dialysis devices, presence of extraneous material, etc.

The sterilization by radiation treatment, in particular gamma radiation, according to known technologies or chemically (aseptic sterilization), the resistance to solvents used in hospitals, non adsorbance of drugs, weldability according to known welding techniques, the dimentional stability are further interesting characteristics of the manufactured articles of the invention.

Further advantages are clear from examples which are given in order to describe and not to limit the invention.

EXAMPLES 1 and 2

Ethylene-propylene copolymers containing 69% (Example 1) and 75% (Example 2) by mols respectively of ethylene have been prepared according to the process described in Italian Patent Application MI-92-A-000666 and above, using a catalytic component obtained from ethylene-bis-(tetrahydroindenyl)-zirconium dichloride and tetraisobutyl-alumoxane. Copolymers obtained show intrinsic viscosities between 2.5 and 3.0 dl/g.

The characterization of copolymers have been carried out on specimens prepared by pressure die-casting, using a cooling speed from 200° C. to room temperature of 40° C./rain in order to approach the cooling generally used in producing manufactured articles. Experimental data are reported in Table 1.

TABLE 1

| Example | 1 | 2 |
|---|---|---|
| Ethylene content (% by mol) | 69 | 75 |
| Ultimate tensile strength[a] (MPa) | 6.7 | 8.5 |
| Ultimate elongation[a] (%) | 650 | 440 |
| Torsional elastic modulus[b] (MPa) | 6.3 | 11.2 |
| Haze[c] (%) | 17 | 29 |
| Shore A[d] | 41 | 46 |
| Tension set[a] (%) | 12 | 16 |

[a] ASTM D412
[b] ASTM D4065
[c] Thickness 1 mm
[d] Reading after 5 seconds

Measure of the torsional elastic modulus has been carried out at a frequency of 10 Hz with a DMTA of Polymer Lab. on specimens 10 mm width, thickness 1.5 mm and length of the useful segment 20 mm.

The suitability of copolymers of examples 1 and 2 for the production of articles for biomedical applications has been experimentally proved by overcoming the following tests, carried out on tubular specimens having inside diameter ID=2.6 mm, outside diameter OD=3.6 mm and thickness t=0.5 mm.

| | |
|---|---|
| Stretching test: | A specimen of length L = 61 cm is stretched by hand until its length is doubled. The overcoming the test is indicated by the absence of "cracks". |
| Knot Test: | A simple knot is produced from a specimen having length about 30.5 cm, free ends are slowly stretched by tighting the knot. At the end of overcoming this test, walls of the tube must not stick to each other in such a way as to block the flow of liquids through the tube itself. |
| Kink Test: | The tube is maintained bent by means of a V type clamp for 6 hours at room temperature and therafter it is freed. The tube must not remain obstructed and must not show bends, nor necks. |

As already said, metals contained in copolymers used in the invention are essentially not extractable by contact with biological fluids, which is particularly advantageous in biomedical applications.

We claim:

1. Shaped articles for biomedical use prepared starting from copolymers of ethylene with propylene and/or alpha olefins $CH_2=CHR$, wherein R is an alkyl containing from 2 to 10 carbon atoms, and optionally with lower proportions of units deriving from a diene or polyene, containing from 45 to 85% by mols of ethylene, from 15 to 55 % by mols of propylene and/or alpha olefins, and from 0 to 10% by mols of diene or polyene, characterized by the following properties:

crystallinity content, measured as melting enthalpy, lower than 20 J/g;

solubility in pentane at 25° C. higher than 90%;

content of propylene units or units deriving from alpha-olefin in form of triads between 4 and 50% of propylene or alpha olefin and percentage of said triads having isotactic structure of at least 70%;

product $r_1 \cdot r_2$ of the reactivity ratio of ethylene, $r_1$, and of propylene or alpha olefin, $r_2$, comprised between 0.4 and 1;

intrinsic viscosity higher than 1.5 dl/g.

2. Shaped articles according to claim 1, wherein the copolymers are characterized by an intrinsic viscosity between 2.5 and 3.0 dl/g.

3. Shaped articles according to claim 1, wherein the copolymers contain from 50 to 75% by mols of ethylene.

4. Shaped articles according to claim 1, wherein the copolymers are characterized by a tension set lower than 30% and an ultimate tensile strength higher than 4 MPa.

5. Shaped articles according to claim 1, wherein the copolymers are characterized by haze values lower than 40%.

6. Shaped articles according to claim 1, wherein the articles are selected from the group consisting of devices for containing, administering, draining or conveying blood and biological fluids, tubes for enteral or parenteral feeding; catheters; syringe seals, and artificial organs.

7. Shaped articles according to claim 1, wherein the articles are selected from the group consisting of devices for containing, administering, draining or conveying blood and biological fluids, tubes for enteral or parenteral feeding, catheters, and syringe seals.

* * * * *